(12) United States Patent
Meyer

(10) Patent No.: US 8,703,741 B2
(45) Date of Patent: Apr. 22, 2014

(54) METHOD OF TREATING ARTICULAR PAIN USING A VANILLOID RECEPTOR AGONIST TOGETHER WITH A GLYCOSAMINOGLYCAN OR PROTEOGLYCAN

(75) Inventor: Dominik Meyer, Zurich (CH)

(73) Assignee: Mestex AG, Zurich (CH)

(*) Notice: Subject to any disclaimer, the term of this patent is extended or adjusted under 35 U.S.C. 154(b) by 706 days.

(21) Appl. No.: 11/722,857

(22) PCT Filed: Dec. 28, 2004

(86) PCT No.: PCT/CH2004/000757
§ 371 (c)(1),
(2), (4) Date: Jun. 26, 2007

(87) PCT Pub. No.: WO2006/069452
PCT Pub. Date: Jul. 6, 2006

(65) Prior Publication Data
US 2008/0153780 A1    Jun. 26, 2008

(51) Int. Cl.
A61K 31/726 (2006.01)
(52) U.S. Cl.
USPC ............................................................. 514/62
(58) Field of Classification Search
USPC ............................................................... 514/62
See application file for complete search history.

(56) References Cited

U.S. PATENT DOCUMENTS

| | | | | |
|---|---|---|---|---|
| 4,801,619 A | * | 1/1989 | Lindblad | 514/42 |
| 5,962,532 A | * | 10/1999 | Campbell et al. | 514/627 |
| 6,689,399 B1 | * | 2/2004 | Dickson | 424/760 |
| 2003/0104085 A1 | * | 6/2003 | Yeomans | 424/760 |
| 2004/0186182 A1 | * | 9/2004 | Burch et al. | 514/625 |
| 2004/0254142 A1 | * | 12/2004 | Kovler | 514/54 |
| 2005/0019436 A1 | * | 1/2005 | Burch et al. | 424/760 |
| 2005/0232980 A1 | * | 10/2005 | Chen | 424/448 |

FOREIGN PATENT DOCUMENTS

| WO | WO03/099013 | * 12/2003 | A01N 65/00 |
|---|---|---|---|
| WO | 2004/056305 | 7/2004 | |

OTHER PUBLICATIONS

Merck Manual Online Medical Library: The Merck Manual for Healthcare Professionals "pain"; also available at http://www.merck.com/mmpe/search.htm last viewed Jan. 14, 2010.*
Merck Manual Online Medical Library: The Merck Manual of Diagnosis and Therapy "pain—Introduction"; also available at http://www.merck.com/mmpe/sec16/ch209/ch209a.html?qt=pain&alt=sh; last viewed Jan. 20, 2010.*
Merriam-Webster's Online Dictionary "derivative"; also available at www.merriam-webster.com/dictionary/derivative; last viewed Jul. 15, 2009.*
Merriam-Webster's Online Dictionary "analogue"; also available at www.merriam-webster.com/dictionary/derivative; last viewed Jan. 20, 2010.*
Merriam-Webster's Online Dictionary "glycosaminoglycan"; also available at www.merriam-webster.com/dictionary/glycosaminoglycan; last viewed Jan. 20, 2010.*
Merriam-Webster's Online Dictionary "proteoglycans"; also available at www.merriam-webster.com/dictionary/proteoglycan; last viewed Jan. 20, 2010.*
Sterner, Olov and Szallasi, Arpad, Trends in Pharmacological Sciences "Novel natural vanilloid receptor agonists: new therapeutic targets for drug development", vol. 20, issue 11, pp. 459-465 (Nov. 1999).*
Bastin, R.J. et al., Organic Process Research and Development, "Salt Selection and Optimisation Procedures for Pharmaceutical New Chemical Entities", vol. 4, issue 5, pp. 427-435 (2000).*
Kuzu, Nevin and Ucar, Hulya, International Journal of Nursing Studies, "The effect of cold on the occurrence of bruising, haematoma and pain at the injection site in subcutaneous low molecular weight heparin", vol. 38, pp. 51-59 (2001).*
Grecomoro, G. et al., Current Medical Research and Opinion, "Therapeutic synergism between hyaluronic acid and dexamethasone in the intra-articular treatment of osteoarthritis of the knee: a preliminary open study", vol. 13, issue 1, pp. 49-55 (1992).*
Sigma-Aldrich, BioUltra Biological Buffers, pp. 1-9; also available at http://www.sigmaaldrich.com/life-science/metabolomics/bioultra-reagents/biological-buffers.printerview.html; last viewed Oct. 4, 2010.*
Marshall, K. W., Current Opinion in Rheumatology, "Intra-articular hyaluronan therapy", 2000, vol. 12, pp. 468-474.*
Pham, T. et al., Ann Rheum Dis, "Evaluation of the symptomatic and structural efficacy of a new hyaluronic acid compound, NRD101, in comparison with diacerein and placebo in a 1 year randomised controlled study in symptomatic knee osteoarthritis", Aug. 2004, vol. 63, pp. 1611-1617.*
"Clinical Significance"; McGraw-Hill Concise Dictionary of Modern Medicine; accessed online from thefreedictionary.com on Jan. 8, 2012.*
Caterina et al. The capsaicin receptor: a heat-activated ion channel in the pain pathway. Nature 389:816-824, 1997.*
Farr et al. Significance of the hydrogen ion concentration in synovial fluid in rheumatoid arthritis. Clin Exp Rheumatol 3:99-104, 1985.*
Karai, L., et al.: "Deletion of vanilloid receptor 1-expressing primary afferent neurons for pain control"; The Journal of Clinical Investigation, United States; vol. 113, No. 9; May 2004; pp. 1344-1352; XP-002333034.

* cited by examiner

*Primary Examiner* — Wu-Cheng Winston Shen
*Assistant Examiner* — Yih-Horng Shiao
(74) *Attorney, Agent, or Firm* — Rankin, Hill & Clark LLP

(57) ABSTRACT

The invention relates to the use of a vanilloid receptor agonist together with a glycosaminoglycan for producing an agent for treating pain.

36 Claims, No Drawings

METHOD OF TREATING ARTICULAR PAIN USING A VANILLOID RECEPTOR AGONIST TOGETHER WITH A GLYCOSAMINOGLYCAN OR PROTEOGLYCAN

The invention relates to the use of a vanilloid receptor agonist together with a glycosaminoglycan or a proteoglycan for producing an agent for the treatment of articular pain of the introductory portion of claim 1 and to a method for applying said agent in the intracapsular space or in the bursa of joints in accordance with the introductory portion of claim 35.

Pain, emanating from joints, frequently has its origin in the area of the joint capsule or in the area of the bone in the vicinity of a joint. In this connection, many analogies may come into consideration, such as arthrotic or arthritic forms of a disease, mechanical or other irritation of bone surfaces in the vicinity of a joint, irritation or injury to the ligament structures of joints, infections, autoimmune processes, etc. In all cases, which are of interest within the scope of this invention, the resulting pain emanates from nociceptive nerve fibers in the region near the joint. Nociceptive nerve fibers are also referred to as C fibers and A delta fibers. If an analgesic substance (such as a local anesthetic or morphine) is injected into a joint so diseased, the symptoms of the patient are alleviated. However, the substances customary at the present time, act for only a limited time, so that the symptoms generally return.

Generally, the following methods are used at the present time for the treatment of painful, diseased joints:
  physiotherapy/movement therapy
  systemic analgesic/antiphlogistic therapy (scepter)
  local analgesic/antiphlogistic methods (etc.)
  surgical methods
  arthroscopic: debridement, joint toilette, etc.
  open/mini-open: joint replacement, joint reinforcement, etc.

A series of known substances for the treatment of painful, inflamed joints has already been proposed in the literature, especially
  osmic acid or radioactive substances, such as technetium 99, which leads to synoviorthesis,
  injection of local anesthetics, hyaluronic acid preparations (etc.)
  injection of antiphlogistic agents
  injection of contrasting agents for joint diagnosis
  joint flushing for joint toilette
  chemical, thermal, electrical or surgical ablation of the nerves, which look after the joints.

All previously used substances and methods lead to only a relatively brief or incomplete freedom from pain or cause lasting damage to the joint.

For example, the known method of synoviorthesis has the disadvantage of destroying the molecular structures, especially of denaturing the proteins, which act as initiators of inflammation in the process of arthritis and, partly also in the development of arthroses. Moreover, a fibrosis of the joint capsules is formed, which is less inflammable and accordingly also less painful. At the same time, due to the fibrosis of the joint, which occurs during the synoviorthesis, the hyperemia, which is generally present and also to be treated, is decreased, also resulting in therapeutic benefit. However, the fibrotic scarring after synoviorthesis may lead to decreased mobility of the joint, as well as to a decreased production of synovial fluid and to the destruction of the joint cartilage. This undesirable fibrosis of the joint capsule should be avoided and only the sensitive innervation of the joint should be switched off.

Furthermore, the injection of capsaicin into the joint for the treatment of pain is known. However, capsaicin by itself has a strong burning effect, produces an inflammation of the joint and damages the cartilage.

The invention is to provide a remedy here. It is an object of the invention to make available an agent for the treatment of articular pain in accordance with the introductory portion of claim 1 and a method for the treatment of articular pain in accordance with claim 35.

Admittedly, the use of precursors (glycosamine) of glycosamino-glycans in a mixture with 10 to 20 different plant products (including also cayenne pepper and capsaicin) in different concentrations for preparing ointments or pastes, which are to be applied on the skin and must be applied at daily, has already been described. However, the herbs, which are contained in this known mixture, have a harmful effect for the objective aimed for here. The use of glycosamines has the further decisive disadvantage that these substances are not required for the integrity of the cartilage, quite in contrast, for example, to the proteoglycan hyaluronic acid. Moreover, for the above-mentioned known uses of the preparation, intended for a surface application on the skin, there are pain-alleviating mechanisms similar to electro-therapy with stimulation of the nerve endings. However, there is no selective denervation of the pain fibers, which is the objective of the invention.

Pursuant to the invention, the objective is accomplished with the use of claim 1 and a method having the distinguishing features of the method of claim 35.

Surprisingly, it was found that the side effects of vanilloid receptor agonists (inflammation and pain during the injection, cartilage damage) can be reduced clearly by the simultaneous administration of glycosaminoglycans or proteoglycans and that the desired effects, such as the liberation from pain, are achieved to a greater extent, then they would be if the substances were administered separately.

This combination permits a metered release of vanilloid receptor agonists and, at the same time, is easy on the joint. Due to the pain-free movement, which takes place once again, the combination has a cartilage-building effect, which is brought about, above all, by the glycosaminoglycan.

The inventive method comprises the local injection of a vanilloid receptor agonist, together with a glycosaminoglycan, preferably without the addition of herb substances or other plant additive, into painful or diseased joints of the body of man or animals. The injected solution may either be left there or, after a certain period of action, be drawn off completely or partly. The glycosaminoglycan partly binds the vanilloid receptor agonist, as a result of which the latter is released more slowly and less pain results. A further effect is that the joint cartilage is not affected adversely, but is built up, and that there are fewer inflammation reactions. The vanilloid receptor agonist diffuses to the sensitive nerve endings, which innervate the region of the joint directly or indirectly, inhibits or damages these predominately and, with that, leads to a reduced perception of joint pain. The two substances together, however, have a synergistic effect for freedom from pain and mobility of the joint.

The effect of the vanilloid receptor agonists (as an analgesic, local or systemic, topical or in the body) is reversible due to healing of the nerves, especially of the C fibers and of the A delta fibers. Due to the addition of substances, which inhibit nerve regeneration (especially of tubulin-binding or microtubulus-binding or other substances), which inhibit the axonal or tubular transport, the effect of the analgesic surprisingly is prolonged.

It is furthermore a novel feature of this method that the joint capsule or the joint bursa is used to concentrate the effect of the mixture (vanilloid receptor agonist with glycosaminoglycan) at the site of the origin of the pain and, by these means, permit a higher local concentration and a longer period of action, then would be possible without the protective joint capsule or the joint bursa at the same concentration and compatibility. At the same time, the vessel and nerve structures and other structures in the vicinity of the joint remain relatively unaffected. Accordingly, a long-term alleviation of the sensation of pain, emanating from the diseased ligament-capsule-joint complex, is achieved by inhibiting or switching off the conduction. This method can be used preventatively or therapeutically.

The advantages of the inventive use of glycosaminoglycans and of vanilloid receptor agonists and of the inventive method for injecting these materials locally into the joint capsule or into the joint bursa, are the following:

- The intraarticular injection of glycosaminoglycans and vanilloid receptor agonists for the analgesic therapy of joints largely takes care of the capsule and ligament structures, the synovia and the cartilage and bone structures and, with that, leads to the maintaining of physiological relationships.
- The utilization of the joint capsule as a natural boundary for the distribution of the glycosaminoglycans and vanilloid receptor agonists.
- The method can be carried out by persons, who are not specialists.
- The method can be carried out with a thin needle, even one that is not an arthroscopic needle.
- The method is not subject to the danger of an infection, in contrast to the popular method of cortisone injections, which greatly promotes the risk of a local infection, since cortisone inhibits the immune system locally.
- The method leads to a sensory denervation, that is, to a switching off of pain-conducting nerves.
- Expansion of joint mobility by eliminating painful movement limitation in contrast to synoviorthosis, for which, because of the capsule fibrosis that results, there is movement limitation.
- Positive preparation for a later arthroplasty, when applied at a joint. Due to the stimulating effect of stressing without pain, which takes place once again, bone formation in the extremity is promoted, especially in the vicinity of the joint, and the bone, in the vicinity of the joint, receives a structure, which is more advantageous for holding a prosthesis at a later time.
- No absorption of fatty tissue (lipolysis).
- No weakening of collagenous tendon, ligament or capsule structures.
- The cartilage is taken care of by the protective action of glycosaminoglycans.
- Due to the highly selective action of vanilloid receptor agonists, there is no myokinetic impairment, no matter where the substance is injected.
- Due to the highly selective action of vanilloid receptor agonists, there is no proprioceptive impairment, no matter where the substance is injected.
- Compared to the known use of glycosamines, the glycosaminoglycans have the advantage that they are components of synovial fluid and of cartilage and have chemical, as well as mechanical functions in the joint. In particular, hyaluronic acid dampens contact forces in the joint and has a lubricating and cushioning property, which the glycosamines do not have. Glycosaminoglycans have the further essential advantage over glycosamines, that glycosaminoglycans are not metabolized further in contrast to glycosamines, which remain in the joint for a significantly longer period of time.

The invention is described in the following for application in man. In particular, the dosages given referred to human administration. However, the invention is also suitable for the veterinary sector, for which the dosages have to be adapted, depending on the body weight of the respective animal.

For a particular embodiment of the invention,
a) herbs or other additional plant additives
b) tricyclic anti-depressants
c) non-anesthetic sodium channel blockers
d) nonsteroidal anti-rheumatic drugs or
e) vasodilators
are not mixed in with the agent.

Due to the omission of herb substances, a pharmacologically usable purity is attained, which facilitates the injection, together with a vanilloid receptor agonist (TRPV1) into the body, allergic or pharmacological side effects are not produced and, at the same time, there is a local denervation of the nerve fibers.

Preferably, the pain treatment is a local treatment and the agent is provided, in particular, for treating the following indications:
a) wound pain after surgery in the form of a flushing solution for intraoperative application for open or arthroscopic or endoscopic surgery, including liposuction;
b) joint pain by intraarticular injection in the case of
   arthrosis
   rheumatoid arthritis
   infectious arthritis
   chondrocalcinosis
   ligamentary damage
   meniscus lesion
   cartilage damage
   synovitis
   arthrofibrosis
   Sudeck's disease
   necrosis of portions of a joint
   neuropathic joint pain
c) bone pain after bone surgery by application on the bone after iliac crest osteotomy or Hallux-Valgus correction
d) bone pain by injection into the bone in the case of necrosis of the head of the femur into the latter or into the body of a vertebra in the case of osteochondrosis;
e) joint stiffness, especially in the case of arthrofibrosis or a frozen shoulder;
f) muscle pain due to intramuscular injection, especially if there is a tear in muscle fibers, if there is pain after muscular exertion or in the case of spastic diseases;
g) painful meniscus, if there is degeneration of or a tear in the meniscus;
h) treatment of back pain by injection into the intervertebral disk in the case of the degeneration of or a tear in the intervertebral disk;
i) painful nerves, especially trigeminus neuralgia, neurinoma, Morton's neurinoma, phantom pain or scar neurinoma;
j) toothache, especially in the case of dental caries, all forms of toothache, before, during or after tooth extraction, before, during or after a tooth is implanted, applied topically in the case of parodontitis, or applied topically in the case of an exposed neck of a tooth;
k) pleuritic complaints
l) intestinal complaints, especially in the case of ulcerous colitis, Crohn's disease, anal fissures or hemorrhoids.

The intra-articular injection of the agent is particularly advantageous.

For a further embodiment, the agent is injected into a synovial cavity, which is not lined with urothel. It has namely turned out that the agent develops its activity ideally on synovial surfaces, but not on the urothel, where ethanol would be required as an additive for developing the activity. However, ethanol is very harmful in the joint.

In particular, agonists for the type 1 receptor (TRPV1) have proven to be advantageous as vanilloid receptor agonists. This group of vanilloids has a particularly low burning effect and, in comparison to substances with a similar potency, such as capsaicin, has hardly any inflammatory or painful side effects when used in combination with glucosaminoglycans or proteoglycans.

The vanilloid receptor agonist may be a capsaicin analog or also a vanilloid, preferably from the group comprising trans-8-methyl-N-vanillyl-6-nonenamides, N-vannillyl-noneamides, beta-aminoethyl-substituted phenyl-alkanamides, methylene-substituted N-phenylmethyl-alkanamides, N-((substituted-phenyl)methyl)-cis-monounsaturated alkenamides, beta-aminoethyl-substituted phenyl compounds, N-((substituted phenyl)methyl)-diunsaturated amides, anandamide, N-oleoyldopamine, trans-capsaicin, cis-capsaicin, civamides, SDZ-249-665, DA-5016, Arvanil, dihydrocapsaicin.

For a preferred embodiment, the vanilloid receptor agonist is a resiniferatoxin compound, preferably resiniferatoxin (RTX), isovelleral, olvanil, phorbol 12,13-didecanoate 20 homovanillates, phorbol 12,13-dinonanoate 20 homovanillates, tinyatoxin, as well as derivatives and salts of the compounds mentioned above. Surprisingly, these substances and, in particular, the resiniferatoxin show an optimum activity profile and significantly fewer side effects. Surprisingly, this is shown particularly clearly in combination with hyaluronic acid as proteoglycan.

Advantageously, the agent should have a concentration between 10 nmolar (nM) and 10 mmolar. The concentration ranges, given for the inventive use, are suitable for achieving a permanent denervation in the joint, when the substance is injected. Due to the special combination of substances, damage to the cartilage, as well as a local inflammation surprisingly can be avoided. In addition, the burning sensation during the injection is reduced. Furthermore, a suitable medium is described in this invention for injecting these substances. The side effects are of a lesser nature at a lower concentration.

Advantageously, the vanilloid receptor agonists should be injected at a concentration or dosage, which is equivalent to the following parameters:
a) in the case of capsaicin as vanilloid receptor agonist, a concentration of 0.05% to 10% by weight or a dose of 0.1 to 200 mg/kg of body weight
b) in the case of resiniferatoxin as vanilloid receptor agonist, a concentration of 1 nM to 100 μM and preferably of 100 to 2000 nM, a dose of 1 ng to 50 μg/kg of body weight or
c) in the case of olvanil, a dose of 0.1 to 200 mg/kg of body weight.

The glycosaminoglycan or proteoglycan may be selected from the following families: keratan, chondroitin sulfate, heparan sulfate, N-keratan sulfate, O-keratan sulfate. It may also be selected from the following substances: decorin, perlecan, dermatan sulfate, serglycine, sydecan, versican, chondroitin sulfate A, chondroitin sulfate B, chondroitin sulfate C and glycosamine sulfate. The dosage for glycosamine sulfate advantageously is 1 to 3,200 mg and typically 10 to 400 mg. The concentration of beta-1-4-glucuronate-beta-1-3-N-acetylglucosamine advisably is 0.1 to 30% by weight of the total solution and preferably 1 to 5%.

For a particularly advantageous mixture, a vanilloid receptor agonist is selected from the family of aggrecanes (preferably resiniferatoxin or beta-1-4-glucuronate-beta-1-3-N-acetylglucosamine) and is used together with hyaluronic acid, preferably with a molecular weight of 1000 to 5000 kDa, their derivatives or salts thereof.

The dosage of the agent advantageously 0.01 mg to 20 g.

The agent should be used without a transdermal carrier liquid. Transdermal preparations are not suitable for injection into the body and the preparation, moreover, is intended to remain in the treated joint and not to defuse out of the joint.

Advantageously, the agent, in a suitable solvent, which is compatible with the body, is injected locally into the pain-affected tissue structure of the patient or applied dropwise locally onto the surgical wound.

For a particular embodiment, the agent may additionally contain a local anesthetic, which results in less pain during the injection. If the concentration is suitably high, the local anesthetics themselves additionally are neurotoxic and support the effect desired.

In a further embodiment, an x-ray contrasting agent, such as a barium salt, or an MRI contrasting agent, is used in addition to the glycosaminoglycan and vanilloid receptor agonist, so that the distribution of the glycosaminoglycan and the vanilloid receptor agonist in the intracapsular space can be checked by an imaging process and, by these means, the distribution in the body can be documented accurately. Depending on the method, the following substances may be used as contrasting agent:

X-ray, CT: Iodine-containing substances, such as triiodinated benzoates or Iopamidol, ideally 30-80 g/100 mL or, for example, 5 to 10% of a different contrasting agent, such as barium MRI: For example, gadolinium, for example, 469.01 mg of gadopentate dimeglumide, 0.99 mg of meglumin, 0.4 mg of dimethylenetriamine pentaacetate per mL.

For a further embodiment, the agent additionally contains a steroid. By these means, inflammation reactions may be suppressed and a synergistic effect achieved with respect to joint pain. The steroid may, for example, be cortisone. Any inflammatory reaction, which may arise, can be controlled therewith. In addition, a more causal treatment of painful, inflammatory joint diseases, which supports the symptomatic, neurolytic therapy, can be added therewith. Betamethasone has proven to be particularly suitable, for example, in the form of 5 mg of betamethasone as dipropionate (crystalline suspension) and 2 mg of betamethasone as disodium phosphate (solution in 1 mL can be added to the amount that is to be injected). This solution is equivalent to 45/23 mg of prednisone/prednisolone.

For a further embodiment, the agent additionally contains a vasoconstrictor, preferably adrenaline, noradrenaline, phenylephrin or ornipressin, preferably alpha-adrenergic vasoconstrictors. By these means, a lower systemic distribution and, with that, a better systemic compatibility and better local effectiveness can be achieved. With adrenaline, it is possible to increase the total dose of the mixture by a factor of approximately 2, since the systemic effect is thus reduced by the decreased absorption. The adrenaline concentration may be 1:10,000 to 1:80,000 to 1:200,000. The total adrenaline dose is less than 0.25 mg. A 50 mL solution of 1:200,000 adrenaline contains 0.25 mg of adrenaline.

The agent advantageously is dissolved in a solvent, which is compatible with the body, preferably, a pharmacologically acceptable vehicle, especially from the group comprising sodium chloride injections solution, Ringer's injection solution, isotonic dextrose, sterile water, dextrose solution, lactated Ringer's injection solution or mixtures thereof. This is essential if the substance mixture is to be injected or if the body region is to be flushed with the substance mixture.

For a further embodiment, the agent additionally contains a permeation promoter, preferably dimethyl sulfoxide, ethoxyethylene diglycol, ethanol, phosphatidyl choline, propylene glycol dipelargonate (DPPG), or glycosylated ethoxylated glycerides. This is of advantage especially for topical application on the skin, but also to improve permeation in tissues and through mucous membranes.

For a further embodiment, an antibiotic, disinfecting and/or sterilizing substance is added additionally to the glycosaminoglycan and vanilloid receptor agonist.

For a further embodiment, the agent additionally contains a calcium salt, by means of which the effectiveness of the vanilloid receptor agonist is improved, since the toxicity is based partly on increasing the intracellular $Ca^{2+}$ level. Advisably, the calcium ion concentration is greater than 2 mmolar and preferably greater than 4 mmolar.

The glycosaminoglycan advisably constitutes 0.5% to 10% and preferably 1.0% to 3.0% of the total mixture. Due to the chondro-protective effect of the glycosaminoglycan, the burning sensation during the injection is suppressed and the joint is taken care of at this range of concentrations. Partial binding of the vanilloid receptor agonist to the glycosaminoglycan may bring about a delayed release over a longer period of time.

For a further embodiment, the agent is dissolved in a buffer solution with a pH above 7.6 and preferably above 8.5. By these means, the burning painfulness during the injection is decreased, since the ion channels of the receptor are opened later.

For a different embodiment, the agent is dissolved in a buffer solution with a pH below 7.2 and preferably below 6.5. By these means, the effect of the vanilloid receptor agonist is increased, since the receptor ion channels open more easily and earlier.

The agent preferably is formulated in a suitable pharmaceutical preparation, which permits a retarded release of the mixture. By these means, the effect can be optimized with fewer side effects.

For a special embodiment, the agent contains a combination of several glycosaminoglycans or proteoglycans. By these means, nerve regeneration is inhibited even more efficiently and with fewer side effects than it would be with only one substance.

For a further embodiment, the agent contains a combination of several vanilloid receptor agonists. Since not all vanilloid receptor agonist dock at or affect the same receptors in the same manner and since they do not all have the same side effect profile, mixtures of such vanilloids may develop advantageous synergies.

The agent is suitable, in particular, for the local treatment of sensations, which are passed on by nerves, which carry vanilloid receptors. Vanilloid receptor agonists damage such nerves highly selectively.

For a special embodiment, the vanilloid receptor agonist locally has a concentration or dosage, which is equivalent to the following parameters;
a) In the case of capsaicin as vanilloid receptor agonist, a concentration of 0.05% to 10% by weight of an appropriate physiological salt solution or a dose of 0.1 to 200 mg/kg of body weight;
b) In the case of resiniferatoxin as vanilloid receptor agonists, a concentration of 5 nM to 500 µM and preferably of 100 to 5000 nM or a dose of 1 ng to 15 mg/kg of body weight and preferably of 10 ng to 50 µg/kg of body weight.

For a further embodiment of the invention, a viscous additive, such as hyaluronic acid, preferably at a concentration of 0.1 to 10.0 mg/mL of injection solution is used in addition to the glycosaminoglycan and the vanilloid receptor agonist. This leads to an improvement in the mechanical sliding of the joint.

For a further embodiment of the invention, a vasoconstrictor is used in addition to the glycosaminoglycan and vanilloid receptor agonist.

For a further embodiment of the invention, a substance with antiphlogistic activity, such as a nonsteroidal antirheumatic agent, a COX-2 inhibitor, acetyl salicylic acid, etc. is used in addition to the glycosaminoglycan and vanilloid receptor agonists.

For a further embodiment of the invention, $Ca^{2+}$ or comparable ions are used in addition to the combination of substances in the solvent at a concentration higher than the physiological concentration and released simultaneously or with delay. Calcium is necessary for the action of the vanilloid receptor agonists and improves their action when present at a hyperphysiological concentration. The concentration of calcium preferably is greater than 2 mmolar and especially greater than 4 mmolar.

For a further embodiment of the invention, a change in the pH is produced at the site of action, preferably by mixing the vanilloid receptor agonists with a suitable, buffered medium. A different activity profile can be produced by shifting the pH. The action of the vanilloid receptor agonist is intensified at a pH below 7.4 and the painfulness of the injection is clearly reduced at a pH above 7.4.

For a further embodiment, therefore, the pH at first is adjusted to a value higher than 7.4 by suitable buffer media, which can also be released with delay by microencapsulation or in solid form, for example, as a powder or as an implant, such as a bone-replacement material. Subsequently, the pH drops, preferably within minutes to hours, to a value below 7.4.

Instead of glycerin, water, salt solution, sodium iothalamate, lophenylate, ricin, polyethylene glycol or polypropylene glycol can be used as solvent. As solvent, glycerin has the advantage that it is hyperbaric and also already somewhat neurotoxic.

Some materials, such as calcium (particularly at a concentration of more than 2 mmolar and preferably of more than 4 mmolar), magnesium, antioxidants, preservatives and excipients, especially sodium bisulfite at a concentration of more than 0.2%, $NaHSO_3$, ammonium compounds, such as ammonium sulfate $(NH_4)_2SO_4$, 2-10 (−30%), polysorbate 80 (PS80) approximately 0.025 mg/milliliter, have proven to intensify the action of the combination of substances.

The glycosaminoglycan with the vanilloid receptor agonist preferably is dissolved in a solvent, which is compatible with the body, and advisably is injected in an amount, which corresponds to the space available in the joint, which is to be treated, so that this joint is filled tightly. With that, the advantage of an optimum local distribution of the glycosaminoglycan with the vanilloid receptor agonist is achieved. It is, however, also possible to inject less liquid, in which case it is advantageous to move the joint well in order to distribute the glycosaminoglycan with the vanilloid receptor agonist better. The maximum liquid volume, to be injected into the intracapsular region, may vary from 0.1 to 150 mL. For a finger joint, a maximum of about 1 mL is sufficient, for the shoulder joint, a maximum of 10 mL, for the knee joint, a maximum of 30 to 50 mL and preferably of not more than 2 mL.

The dosage of the combination of substances depends on the localization and indication.

The agent advantageously is injected locally into the pain-affected tissue structure of the patient in a suitable solvent, which is compatible with the body, or applied dropwise locally on to the surgical wound, applied at a peripheral nerve or applied suitably transcutaneously.

For a preferred method, the agent is injected locally into the intracapsular region or into the bursa of a joint affected by pain. The agent may be dissolved in a solvent, which is compatible with the body and of which preferably 0.1 to 150 mL are injected into the intracapsular region or into the bursa of the joint affected by pain. The nociceptive nerve fibers are made insensitive to pain by these means for at least 14 days and preferably for at least 8 weeks.

The agent preferably is used at such a concentration, that neurolysis occurs

The agent may be administered locally, regionally, systemically (intravenously, perorally, subcutaneously, intramuscularly etc.) or topically on the skin or mucous membranes.

For a special method, the vanilloid receptor agonist and the glycosaminoglycan or proteoglycan are used simultaneously. A good local control and few side effects can be achieved by these means. In particular, a good local and temporally synergistic effect of the two substances is achieved.

For a different method, the vanilloid receptor agonist is used first, after which the glycosaminoglycan or proteoglycan is used. By these means, the vulnerable phase of nerve regeneration can be utilized better in some situations and a more efficient effect can be achieved.

For a different embodiment, the glycosaminoglycan or proteoglycan is used first, after which the vanilloid receptor agonist is used. By these means, the vulnerable phase of nerve regeneration can be utilized better in some situations and a more efficient effect can be achieved.

For a different method, the can also be used repetitively is used first, followed by the vanilloid receptor agonist. For some situations, the vulnerable phase of nerve regeneration can be utilized better by these means and a more efficient effect is achieved.

The vanilloid receptor agonist and/or the glycosaminoglycan or proteoglycan can also be used repetitively. By these means, the vulnerable phase of nerve regeneration can be utilized better in some situations and a more efficient effect can be achieved.

Finally, the vanilloid receptor agonist and/or the glycosaminoglycan or proteoglycan can be used with retarded release. By these means, the vulnerable phase of nerve regeneration can be utilized better in some situations and a more efficient effect can be achieved. The local and systemic side effects of the two substances can be reduced decisively in this way.

For a special embodiment, the joint, which is to be treated, is cooled before the application of the agent, in order to reduce pain. As a result, less pain develops during the injection or application of the mixture of substances, since the vanilloid-sensitive ion channels open more slowly at lower temperatures.

For a different embodiment, a local anesthetic is used in addition, either simultaneously with the agent or before the agent is administered. By these means, it is achieved that the injection or application is not painful. The local anesthetic may be injected at the same place as the agent or remote therefrom. By these means, local pain during the injection can be decreased.

Moreover, the invention is carried out in greater detail by means of numerous examples.

EXAMPLE 1

Under the optionally simultaneous (image converter, CT, sonography, MRI, etc.) or subsequent (x-ray, CT, MRI, sonography, arthroscopy, etc.) imaging control, the therapist brought an injection needle into the articular space of a knee joint and injected 9 mL of a 500 nmolar solution (approximately 0.003 mg) with 1% (approximately 90 mg) of hyaluronic acid into the intracapsular space. The patient noted a clear alleviation of his symptoms already 14 hours after the intervention. This alleviation lasted for more than 6 months.

EXAMPLE 2

Under the optionally simultaneous (image converter, CT, sonography, MRI, arthroscopy, etc.) or subsequent (x-ray, CT, MRI, sonography, etc.) imaging control, the therapist brought an injection needle into the articular space of a knee joint and injected 9 mL of a 500 nmolar solution (approximately 0.003 mg) of resiniferatoxin with 0.03 mg of Vincristin and 1% (approximately 90 mg) of hyaluronic acid into the intracapsular space. The patient noted a clear alleviation of his symptoms already within 14 hours of the intervention. This alleviation lasted for more than 9 months.

EXAMPLE 3

The injected solution corresponded to that of Example 1 with the difference that, for the imaging method to be used, 5 mL of a visible contrasting agent (lopamidol) was added at a concentration of 50 g/100 mL. After the injection, this contrasting agent spread out within the joint capsule and thus documented the position of the injection needle and the distribution of the 500 nM (approximately 0.003 mg) solution of resiniferatoxin with 1% (approximately 90 mg) hyaluronic acid in the joint capsule. This solution was drawn off again immediately after the injection. It could, however, also be drawn off after a defined, substance-dependent time of action or not be drawn off at all. The patient noted a clear alleviation of his symptoms already 15 hours after the intervention. This alleviation lasted for more than 8 months.

EXAMPLE 4

The therapist placed a thin infusion catheter, similar to an epidural catheter, into the affected joint and, with a perfuser, injected a mixture of 2 liters of a 100 nmolar solution of resiniferatoxin with 1% hyaluronic acid into the affected joint at a rate of 1-10 mL/h for 12 hours. Optionally, he also placed a drainage catheter with an optionally defined drainage resistance (such as 20 mm Hg), in order to achieve a liquid turnover. With this method, the therapist achieved a uniform infiltration of the painful joint, without large concentration peaks. Moreover, it was possible to define the period of action better.

During subsequent arthroscopies after 1, 2, 7, 14 and 28 days, it was possible to show that only a very little inflamed tissue was present. The patient noted a clear alleviation of his symptoms already 12 hours after the intervention. This alleviation lasted for more than one year.

EXAMPLE 5

After a knee joint prosthesis had been implanted, the therapist injected 20 mL of a mixture of 500 nmolar (approximately 0.006 mg) of resiniferatoxin with 20 mg of hyaluronic acid into the joint capsule, which had been closed off once again. It was possible to minimize postoperative pain by these means.

EXAMPLE 6

After a hip joint prosthesis had been implanted, the therapist injected 10 mL of a mixture of 500 nmolar (approximately 0.003 mg) solution of resiniferatoxin with 20 mg of hyaluronic acid and 0.01 mg of Vincristin into the periprosthetic region without a capsule. It was possible to minimize postoperative pain by these means.

EXAMPLE 7

A 500 nmolar solution (approximately 0.003 mg) of resiniferatoxin with 0.01 mg of Vincristin was injected into the (neo)-capsule about the prosthesis of a patient with a painful, septic loosening of a total hip endoprosthesis. Subsequently, the patient experienced a permanent (more than one year) alleviation of pain within a few (6-12) hours. In addition, the infection about the prosthesis was brought very much under control by the diffusion of the analgesic (which also had antiseptic activity) along the shaft of the prosthesis and about the socket and, in some cases, was even eliminated completely. Optionally, this treatment may be supported with systemically administered antibiotics (such as 450 mg of Rifampicin, 750 mg of ciprofloxacin). It was possible to show radiologically that the bone substance had consolidated about the prosthesis.

EXAMPLE 8

Under the optionally simultaneous (image converter, CT, sonography, MRI, etc.) or subsequent (x-ray, CT, MRI, sonography, arthroscopy, etc.) imaging control, the therapist brought an injection needle in the joint space of a knee joint and injected 10 mL of a 500 μM solution (approximately 0.003 mg) of resiniferatoxin with 60 mg of hyaluronic acid, buffered to a pH of 8.6, into the intracapsular space. The patient noted a clear alleviation of his symptoms already a few minutes after the intervention. This alleviation lasted for more than 6 months.

EXAMPLE 9

Under the optionally simultaneous (image converter, CT, sonography, MRI, etc.) or subsequent (x-ray, CT, MRI, sonography, arthroscopy, etc.) imaging control, the therapist, after optional prior local anesthesia, for example with lidocaine, brought an injection needle into the joint space of a knee joint and injected 20 mL of a 500 nmolar solution (approximately 0.007 mg) of resiniferatoxin with 200 mg of glycosamine sulfate in a physiological salt solution into the intracapsular space. The patient noted a distinct alleviation of his symptoms already within minutes of the intervention. This alleviation lasted for more than 6 months.

EXAMPLE 10

Under the optionally simultaneous (image converter, CT, sonography, MRI, etc.) or subsequent (x-ray, CT, MRI, sonography, arthroscopy, etc.) imaging control, the therapist brought an injection needle into the joint space of a knee joint and injected 20 mL of a solution of 0.007 mg of resiniferatoxin with 400 mg of glycosamine sulfate in a physiological salt solution into the intracapsular space. The patient noted a clear alleviation of his symptoms already a few minutes after the intervention. This alleviation lasted for more than 6 months.

EXAMPLE 11

Under optional local analgesia and optional simultaneous (image converter, CT, sonography, MRI, etc.) or subsequent (x-ray, CT, MRI, sonography, arthroscopy, etc.) imaging control, the therapist brought an injection needle into the joint space of a knee joint and injected 20 mL of a 1 μM tinyatoxin solution with 800 mg of glycosamine sulfate and 0.3 mg of taxol in physiological salt solution, buffered to a pH of 5 with 8 mM $Ca^{2+}$ into the intracapsular space. The patient noted a clear alleviation of his symptoms already a few minutes after the intervention. This alleviation lasted for more than 8 months.

EXAMPLE 12

The one mixture of a 500 nM solution (approximately 0.003 mg) of resiniferatoxin with 20 mg of hyaluronic acid in a physiological salt solution was injected into the joint of a patient with a painful capsulitis of joints (such as a frozen shoulder). Once again, it was possible to check the distribution of the substance visually by adding an appropriate contrasting agent. Optionally, a substance with antiphlogistic activity was admixed. A few minutes after the injection, the pain was alleviated permanently, so that the patient regained the mobility, lost due to the capsulitis, by undergoing physiotherapy. For this application, only a temporary analgesia (2-3 weeks) is sometimes required, so that the concentration of the neurotoxic substance, if anything, was kept low here.

EXAMPLE 13

The joint of a patient with painful capsulitis of joints was injected with a mixture of 0.008 mg of resiniferatoxin with 20 mg of hyaluronic acid in a physiological salt solution. The pain was alleviated permanently a few minutes after the injection, so that the patient recovered the mobility, lost due to the capsulitis, by undergoing physiotherapy.

EXAMPLE 14

The therapist injected 5 mL of a 500 nmolar solution (approximately 0.002 mg) of resiniferatoxin with 20 mg of hyaluronic acid and glycerin as solvent into a chronically inflamed Bursa trochanterica above the Trochanter major of the hip. Within 60 minutes, the symptoms of the patient disappeared and the patient remained asymptomatic at this place for several years.

EXAMPLE 15

The therapist injected 0.5 mL of a 500 nmolar solution (approximately 0.00001 mg) of resiniferatoxin with 5 mg of hyaluronic acid and 5% of contrasting agent in a physiological salt solution as solvent into a painful, arthrotic finger joint. After about 15 minutes, the symptoms of the patient disappeared for several months. It was possible to document the correct position of the injection needle by means of the contrasting agent.

The invention claimed is:

1. A method for reducing articular pain in a human being, the method comprising administering a mixture locally to a joint affected by pain via intra-articular injection, wherein the mixture comprises:

a vanilloid receptor agonist selected from the group consisting of capsaicin, trans-8-methyl-N-vanillyl-6-nonenamides, N-vannillyl-noneamides, beta-aminoethyl-substituted phenyl-alkanamides, methylene-substituted N-phenylmethyl-alkanamides, N-((substituted-phenyl) methyl)-cis-monounsaturated alkenamides, beta-aminoethyl-substituted phenyl compounds, N-((substituted phenyl)methyl)diunsaturated amides, anandamide, N-oleoyldopamine, transcapsaicin, cis-capsaicin, civamides, SDZ-249-665, DA-5016, Arvanil, dihydrocapsaicin, resiniferatoxin, beta-1-4-glucuronate-beta-1-3-N-acetylglucosamine, isovelleral, olvanil, phorbol 12,13-didecanoate 20 homovanillate, phorbol 12,13-dinonanoate 20 homovanillate, and tinyatoxin; and a glycosaminoglycan or proteoglycan selected from the group consisting of keratan, chondroitin sulfate, heparan sulfate, N-keratan sulfate, O-keratan sulfate, decorin, perlecan, dermatan sulfate, serglycine, sydecan, versican, and hyaluronic acid;

wherein the vanilloid receptor agonist and the glycosaminoglycan or proteoglycan are dissolved in a solvent, which is compatible with the human being, to form the mixture, wherein a concentration of the vanilloid receptor agonist is between 10 nanomolar (nM) and 10 mmolar, and wherein the glycosaminoglycan or proteoglycan constitutes 0.5% to 10% of the mixture by weight.

2. The method of claim 1, wherein the mixture does not contain any herbs or other additional plant additives.

3. The method of claim 1, wherein no tricyclic antidepressant is administered.

4. The method of claim 1, wherein no non-anesthetic sodium channel blocker is administered.

5. The method of claim 1, wherein no vasodilator is administered.

6. The method of claim 1, wherein the mixture is administered to treat arthrosis, rheumatoid arthritis, infectious arthritis, chondrocalcinosis, ligamentary damage, meniscus lesion, cartilage damage, synovitis, arthrofibrosis, Sudeck's disease, necrosis of portions of a joint, or neuropathic joint pain.

7. The method of claim 1, wherein the vanilloid receptor agonist is an agonist for the type 1 receptor (TRPV1).

8. The method of claim 1, wherein the vanilloid receptor agonist locally has a concentration or dosage, which is equivalent to the following parameters:
a) in the case of capsaicin as the vanilloid receptor agonist, a concentration of 0.05% to 10% by weight or a dose of 0.1 to 200 mg/kilogram of body weight;
b) in the case of resiniferatoxin as the vanilloid receptor agonist, a concentration of up to 100 µM or a dosage of 1 ng to 50 µg/kilogram of body weight; or
c) in the case of olvanil as the vanilloid receptor agonist, a dose of 0.1 to 200 mg/kilogram of body weight.

9. The method of claim 1, wherein a dosage of the mixture is 0.01 mg to 20 g.

10. The method of claim 1, wherein the mixture is used without a transdermal carrier liquid.

11. The method of claim 1, wherein the mixture additionally contains a local anesthetic.

12. The method of claim 1, wherein the mixture additionally contains an x-ray contrasting agent.

13. The method of claim 1, wherein the mixture additionally contains a steroid.

14. The method of claim 1, wherein the mixture additionally contains a vasoconstrictor.

15. The method of claim 1, wherein the mixture additionally contains a permeation promoter.

16. The method of claim 1, wherein the mixture additionally contains a calcium salt.

17. The method of claim 16, wherein the calcium ion concentration is greater than 2 mmolar.

18. The method of claim 1, wherein the vanilloid receptor agonist and the glycosaminoglycan or proteoglycan are dissolved in a buffer solution with a pH above 7.6.

19. The method of claim 1, wherein the vanilloid receptor agonist and the glycosaminoglycan or proteoglycan are dissolved in a buffer solution with a pH below 7.2.

20. The method of claim 1, wherein the mixture is formulated in a suitable pharmaceutical preparation, which permits a retarded release of the mixture.

21. The method of claim 1, wherein the mixture contains a combination of two or more of said glycosaminoglycans or proteoglycans.

22. The method of claim 1, wherein the mixture contains a combination of two or more of said vanilloid receptor agonists.

23. The method of claim 1 wherein the mixture locally treats sensations, which are passed on by nerves, which carry vanilloid receptors.

24. The method of claim 1, wherein the vanilloid receptor agonist locally has a concentration or dosage, which is equivalent to the following parameters:
a) in the case of capsaicin as the vanilloid receptor agonist, a concentration of 0.05% to 10% by weight of an appropriate physiological salt solution or a dose of 0.1 to 200 mg/kilogram of body weight; and
b) in the case of resiniferatoxin as the vanilloid receptor agonist, a concentration of up to 500 µM or a dose of 1 ng to 15 mg/kilogram of body weight.

25. A method for reducing articular pain in a human being, the method comprising injecting a mixture comprising
i) a vanilloid receptor agonist; selected from the group consisting of capsaicin, trans-8-methyl-N-vanillyl-6-nonenamides, N-vannillyl-noneamides, beta-aminoethyl-substituted phenyl-alkanamides, methylene-substituted N-phenylmethyl-alkanamides, N-((substituted-phenyl)methyl)-cis-monounsaturated alkenamides, beta-aminoethyl-substituted phenyl compounds, N-((substituted phenyl)methyl)-diunsaturated amides, anandamide, N-oleoyldopamine, trans-capsaicin, cis-capsaicin, civamides, SDZ-249-665, DA-5016, Arvanil, dihydrocapsaicin, resiniferatoxin, beta-1-4-glucuronate-beta-1-3-N-acetylglucosamine, isovelleral, olvanil, phorbol 12,13-didecanoate 20 homovanillate, phorbol 12,13-dinonanoate 20 homovanillate, and tinyatoxin, and
ii) 0.5% to 10% by weight of the mixture of a glycosaminoglycan or a proteoglycan selected from the group consisting of keratan, chondroitin sulfate, heparan sulfate, N-keratan sulfate, O-keratan sulfate, decorin, perlecan, dermatan sulfate, serglycine, sydecan, versican and hyaluronic acid, locally into the intracapsular region or into the bursa of a joint affected by pain.

26. The method of claim 25, wherein the vanilloid receptor agonist and the glycosaminoglycan or proteoglycan are dissolved in a solvent, which is compatible with the human being, to form a solution, and a volume of 0.1 to 150 mL of the solution is injected into the intracapsular region or into the bursa of the joint affected by pain.

27. The method of claim 25, wherein subsequent to injection of the vanilloid receptor agonist and the glycosaminoglycan or proteoglycan, nociceptive fibers are made insensitive to pain for at least 14 days.

28. The method of claim 25, wherein subsequent to injection of the vanilloid receptor agonist and the glycosaminoglycan or proteoglycan, neurolysis occurs.

29. The method of claim 25, wherein the vanilloid receptor agonist and the glycosaminoglycan or proteoglycan are injected repetitively.

30. The method of claim 25, wherein the vanilloid receptor agonist and the glycosaminoglycan or proteoglycan are used with retarded release.

31. The method of claim 25, wherein the joint, which is to be treated, is cooled before the vanilloid receptor agonist and the glycosaminoglycan or proteoglycan is injected.

32. The method of claim 25, wherein a local anesthetic is used in addition, either simultaneously with the injection of the vanilloid receptor agonist and the glycosaminoglycan or proteoglycan, or before the vanilloid receptor agonist and the glycosaminoglycan or proteoglycan are injected.

33. The method of claim 32, wherein the local anesthetic is injected at the same place as the vanilloid receptor agonist and the glycosaminoglycan or proteoglycan, or at a place remote therefrom.

34. A method for reducing articular pain in a human being, the method comprising administering a mixture locally to a joint affected by pain via intra-articular injection, wherein the mixture comprises:
   a vanilloid receptor; and
   a glycosaminoglycan; and
   wherein the vanilloid receptor agonist is resiniferatoxin,
   wherein the vanilloid receptor and the glycosaminoglycan dissolved in a solvent, which is compatible with the human being, to form the mixture, and
   wherein the glycosaminoglycan constitutes 0.5% to 10% of the mixture by weight.

35. The method according to claim 34 wherein the glycosaminoglycan is hyaluronic acid.

36. The method according to claim 35 wherein the hyaluronic acid has a molecular weight of 1000 to 5000 kDa.

\* \* \* \* \*